US010088411B2

United States Patent
Shyam et al.

(10) Patent No.: US 10,088,411 B2
(45) Date of Patent: Oct. 2, 2018

(54) METHOD AND DEVICE FOR PERFORMING COLORIMETRIC ANALYSIS OF A TEST FLUID TO EVALUATE PHYSIOLOGICAL PARAMETERS

(71) Applicant: RENALYX HEALTH SYSTEMS PVT LTD, Bangalore, Karnatraka (IN)

(72) Inventors: Vishnu Shyam, Bangalore (IN); Mahabaleswara R. Bhatt, Bangalore (IN); Manav Singal, Bangalore (IN); Kishin Gandhi, Bangalore (IN)

(73) Assignee: Renalyx Health Systems Pvt Ltd., Bangalore (IN)

( * ) Notice: Subject to any disclaimer, the term of this patent is extended or adjusted under 35 U.S.C. 154(b) by 0 days.

(21) Appl. No.: 15/550,299

(22) PCT Filed: Feb. 4, 2016

(86) PCT No.: PCT/IB2016/050558
§ 371 (c)(1),
(2) Date: Aug. 10, 2017

(87) PCT Pub. No.: WO2016/132243
PCT Pub. Date: Aug. 25, 2016

(65) Prior Publication Data
US 2018/0024049 A1    Jan. 25, 2018

(30) Foreign Application Priority Data
Feb. 19, 2015 (IN) .............................. 791/CHE/2015

(51) Int. Cl.
*G01N 21/25* (2006.01)
*G01N 21/78* (2006.01)

(52) U.S. Cl.
CPC ......... *G01N 21/255* (2013.01); *G01N 21/251* (2013.01); *G01N 21/78* (2013.01)

(58) Field of Classification Search
CPC ...... G01J 3/51; G01J 3/513; G01J 3/50; G01J 3/46; G01J 3/02
(Continued)

(56) References Cited

U.S. PATENT DOCUMENTS

2005/0099506 A1* 5/2005 Stokes .................... H04N 1/62
348/223.1
2011/0293153 A1   12/2011 Plickert et al.
(Continued)

FOREIGN PATENT DOCUMENTS

EP        1963828 A1    9/2008
WO    2014/002541 A1    1/2014

OTHER PUBLICATIONS

International Search Report and Written Opinion for Application No. PCT/IB2016/050558, dated May 27, 2016, 16 pages.
(Continued)

*Primary Examiner* — Md M Rahman
(74) *Attorney, Agent, or Firm* — Sheppard Mullin Richter & Hampton LLP (57) ABSTRACT

The present disclosure relates to a method and a calorimetric device for performing colorimetric analysis of a test fluid to evaluate associated physiological parameters. The images of the test strip at different heights are captured by the calorimetric device and based on analysis of the captured images, a plurality of geometric parameters respectively associated with the test strip is determined. Based on the plurality of geometric parameters, an image resizing factor is determined and resized images are generated based on the image resizing factor. Upon generating the resized images, calorimetric values respectively associated with the resized images are determined based on which physiological parameters associated with the test fluid are evaluated.

14 Claims, 7 Drawing Sheets

(58) Field of Classification Search
USPC .......................................................... 356/406
See application file for complete search history.

(56) References Cited

U.S. PATENT DOCUMENTS

| | | | |
|---|---|---|---|
| 2013/0183772 A1* | 7/2013 | Fleming | G01N 21/8483 |
| | | | 436/501 |
| 2013/0222634 A1 | 8/2013 | Setlur et al. | |
| 2014/0154789 A1 | 6/2014 | Polwart et al. | |
| 2015/0055134 A1* | 2/2015 | Papautsky | G01N 21/25 |
| | | | 356/408 |
| 2015/0099949 A1* | 4/2015 | Wallace | A61B 5/742 |
| | | | 600/323 |

OTHER PUBLICATIONS

International Preliminary Report on Patentability for Application No. PCT/IB2016/050558, dated May 10, 2017, 13 pages.
Cadle, B. et al., "Cellular Phone-Based Image Acquisition and Quantitative Ratiometric Method for Detecting Cocaine and Benzoylecgonine for Biological and Forensic Applications," Substance Abuse: Research and Treatment, Sep. 2010, vol. 21, p. 21-33.
Tippkotter, N. et al., "A semi-quantitative dipstick assay for microcystin," Analytical and Bioanalytical Chemistry, Jun. 2009, vol. 394, No. 3, p. 863-869 (Abstract only).

\* cited by examiner

METHOD AND DEVICE FOR PERFORMING COLORIMETRIC ANALYSIS OF A TEST FLUID TO EVALUATE PHYSIOLOGICAL PARAMETERS

CROSS-REFERENCE TO RELATED APPLICATIONS

The present application is a National Phase Application of International Application No. PCT/IB2016/050558, filed on Feb. 4, 2016, which claims priority to and benefit of India Patent Application No. 791/CHE/2015, filed on Feb. 19, 2015. Both of the above-referenced applications are incorporated into the present application by reference herein in their entirety.

FIELD OF THE DISCLOSURE

The present subject matter is related, in general to colorimetric analysis, and more particularly, but not exclusively to a method and a device for performing colorimetric analysis of a test fluid to evaluate associated physiological parameters.

BACKGROUND

The need of accurate and quick but affordable diagnostic medical devices with mobility is becoming more important for routine or periodic check up in a person's busy life. In this perspective, several personal electronic devices that are communication or infotainment oriented have been exploited to be used as health care monitoring device. Few examples of electronic devices may include Smartphone, tablet etc. These electronic devices are becoming cheaper by the day and also possess enormous capability for computing due to the application of multi-core CPU, high resolution and high dynamic range of camera, sufficient storage, wireless communication and excellent quality display.

On the other hand, the need of quick monitoring of sugar or salt contents in bodily fluid like urine and blood as a bio marker in routine is inevitable to have preventive care for health conditions. One of the popular, inexpensive and quick methods is paper micro-fluidic assay based Point of Care (POC) devices. In the POC devices, the diagnostic health parameters are derived from colorimetric parameters of assay. Currently, the colorimetric analysis is performed by an instrument using color analyzer or customized video camera with a computer. However, presently there is no affordable, mobile and self-diagnostic care instrument.

Few challenges associated with consistent quantitative measurement using a Smartphone or tablet is mentioned herein. The consistent quantitative determination of colorimetric parameters needs to be optimized for photography in ambient conditions, since the color image is highly dependent on ambient lighting or flash lighting conditions. Further, the resolution of the image captured in any camera system is dependent not only on focusing and lighting conditions, but also on the distance at which the image is captured. This raises the issue of imaging at known height or at same height which is difficult to assure or otherwise restrict the usage only to trained experts. The need of low power consumption is another issue that restricts computations that are needed for geometric image analysis for colorimetry. In addition, the evaluation of small color changes in the POC color paper assay is difficult. This is because capturing minor level chemical changes in the POC color paper assay before and after dipping into the bodily fluid in question by the Smartphone or tablet camera optics may not be accurate. Further, the calorimetric calibration of the POC color strip that are mentioned on the assay may not hold accurately though these calibrations are carried out in factory controlled environment. This is because the colorimetric parameters naturally drift due to aging of color. Therefore, there is a need for a method and a device for performing colorimetric analysis of a test fluid to evaluate associated physiological parameters.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

Accordingly, the present disclosure relates to a method of performing colorimetric analysis of a test fluid to evaluate associated physiological parameters. The method comprising the step of receiving a first image of a test strip captured at a first height before dipping the test strip into the test fluid, and a second image of the test strip captured at a second height after dipping the test strip into the test fluid. Based on analysis of the captured first and second images, a plurality of first and second geometric parameters respectively associated with the test strip is determined. The method further comprising the step of deriving an image resizing factor based on the plurality of first and second geometric parameters and generating one of a resized first image and a resized second image based on the image resizing factor thus derived. Upon generating the resized first and second images, first and second calorimetric values respectively associated with the resized first and the resized second images are determined. Based on the first and second calorimetric values and one or more determined calorimetric values, a change in luminosity is determined based on which one or more physiological parameters associated with the test fluid are evaluated.

Further, the present disclosure relates to a system for performing colorimetric analysis of a test fluid to evaluate associated physiological parameters. The system comprises at least an image capturing device configured to capture one or more images of a test strip and a processor coupled with the image capturing device. The system further comprises a memory communicatively coupled with the processor, wherein the memory stores processor-executable instructions, which, on execution, cause the processor to receive a first image of the test strip captured by the image capturing device at a first height before dipping the test strip into the test fluid, and a second image of the test strip captured at a second height after dipping the test strip into the test fluid. Based on the plurality of first and second geometric parameters, the processor is configured to derive an image resizing factor and generate one of a resized first image and a resized second image based on the image resizing factor thus derived. The processor is further configured to determine a first and second calorimetric value respectively associated with the resized first and the resized second image. Based on first and second calorimetric value and determined calorimetric values, the processor is configured to determine a change in luminosity and evaluate one or more physiological parameters associated with the test fluid based on the change in luminosity thus determined.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed embodiments. In the figures, the leftmost digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however, that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

The present disclosure relates to a calorimetric device and a method of performing colorimetric analysis of a test fluid to evaluate associated physiological parameters. In one embodiment, the calorimetric device comprises an image capturing device configured to capture first and second images of a test strip at one or more heights before or after dipping the test strip in the test fluid. Based on the analysis of the captured first and second images of the test strip, the calorimetric device determines one or more geometric parameters associated with the test strip based on which an image resizing factor is determined. The calorimetric device further generates a resized first image and a resized second image using the image resizing factor based on which one or more calorimetric values associated with the resized first and second images is determined. A plurality of device dependent pixel values of the resized first and second images are determined by the calorimetric device based on RGB pixel values derived from the resized first and second images using normalization and gamma correction techniques. An intensity value for each normalized RGB pixel values is computed for each derived RGB pixel values to determine linearized gamma corrected device dependent RGB pixel values based on predetermined gamma correction factor, thus reducing the computations to determine the gamma correction factor each time.

Upon determining, the plurality of device dependent pixel values are converted into corresponding plurality of device independent pixel values. The calorimetric device then determines a change in luminosity based on determined calorimetric values and predetermined calorimetric values based on which the calorimetric device generates a calorimetric curve. The newly generated calorimetric curve indicates the changes in the physiological parameters associated with the test fluid from manufacturing time to the time of using the test strip. Thus, the calorimetric device and associated method enables efficient computation of calorimetric values and calorimetric curve of the test strip to determine the physiological parameters involving less number of computations and storage memory.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1A:
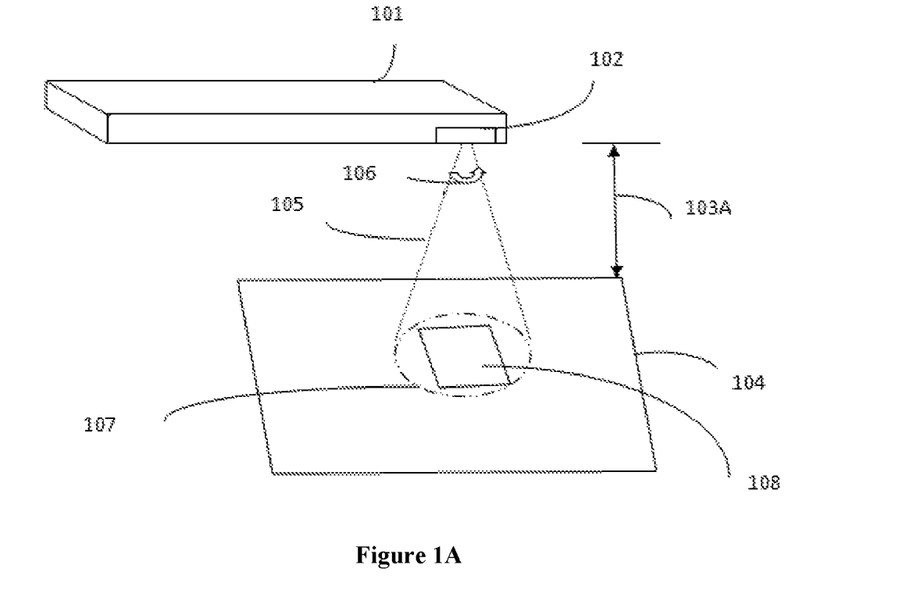
FIGS. 1A, 1B and 1C illustrate an exemplary embodiment of a calorimetric device for capturing image of test strip in accordance with some embodiment of the present disclosure.
Figure 1B:
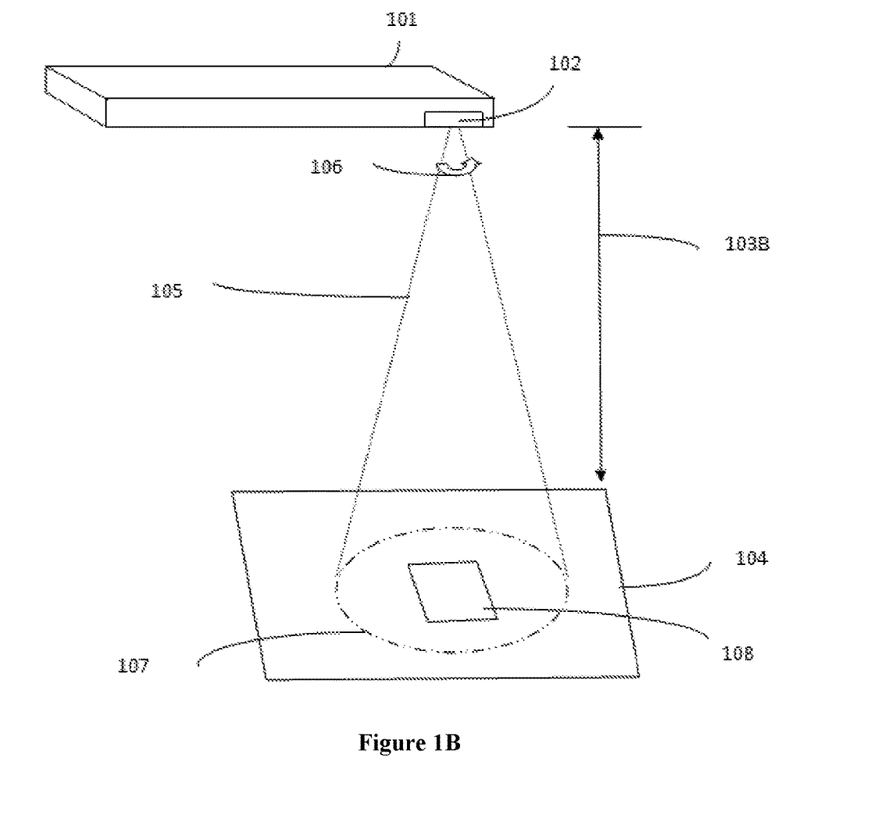
Figure 1C:
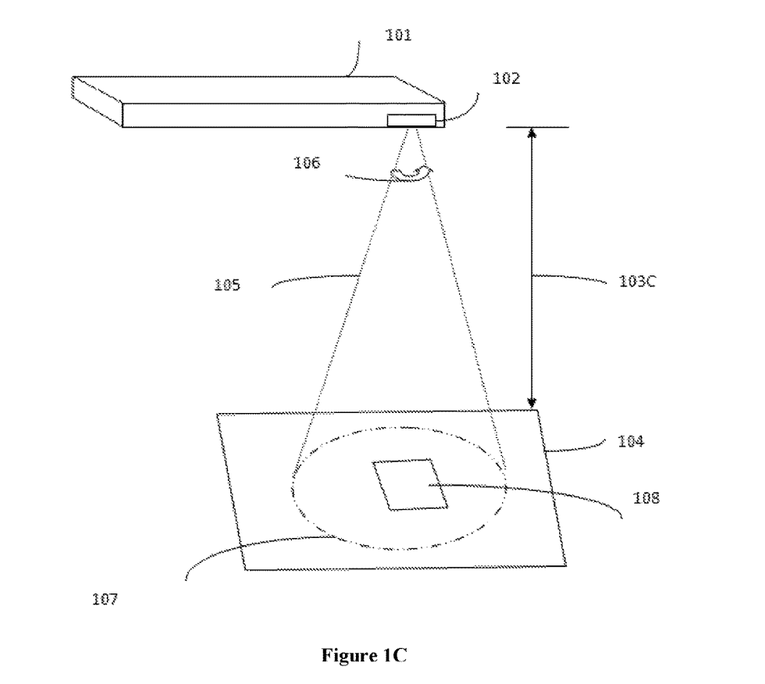

FIGS. 1A, 1B and 1C illustrate an exemplary embodiment of a calorimetric device for capturing images of a test strip in accordance with some embodiment of the present disclosure. FIG. 1A illustrates the calorimetric device 101 configured with an image capturing device or image sensor 102 such as camera. The calorimetric device 101 may be an electronic device configured to perform calorimetric analysis based on the images of the test strip captured by the image sensor 102. As an example, the electronic device can be any device capable of capturing images, processing the image and providing display. The electronic device may include, but not limited to, smart phone, tablet and Personal Digital Assistant (PDA) etc. In another example, the electronic device may be a handheld portable device.

The calorimetric device 101 is positioned at a first height or distance 103A from a background 104 that is holding the test strip. The image sensor 102 flashes light with light rays 105 on the POC color strip alternatively referred as assay or test strip on the top surface of the test strip 108. In another embodiment, an external light source may be used for flashing light on the test strip 108. The light rays 105 from the image sensor 102 or the external light source have a solid angle of exposure 106. The calorimetric device 101 is configured to capture a first image of the test strip 108 via the image sensor 102 positioned at the first height and obtain calibration curve with 3-D chromaticity model using data associated with the captured first image. The first image, the calibration curve and data associated with the first image are stored in memory and printed and/or supplied as specification corresponding to the POC assay for future use.

In another embodiment, the calorimetric device 101 is positioned at a second height or distance 103B from the background 104 just before using the test strip 108 for analysis as illustrated in FIG. 1B. FIG. 1B illustrates a similar embodiment as FIG. 1A. The calorimetric device 101 is configured to capture the second image of the test strip via the image sensor 102 positioned at the second height and obtain calibration curve with 3-D chromaticity model using data associated with the captured second image. The second image, the calibration curve and data associated with the second image are stored in memory and printed and/or supplied as specification corresponding to the POC assay for future use. In one embodiment, the second height 103B is more than the first determined height 103A.

FIG. 1C illustrates an embodiment of image capturing of the given test strip after dipping or soaking with test fluid associated with a person for evaluating physiological parameters of the person. The test strip 108 is dipped or soaked in the test fluid that changes corresponding colorimetric values that yields physiological parameters associated with the test fluid.

Figure 2:
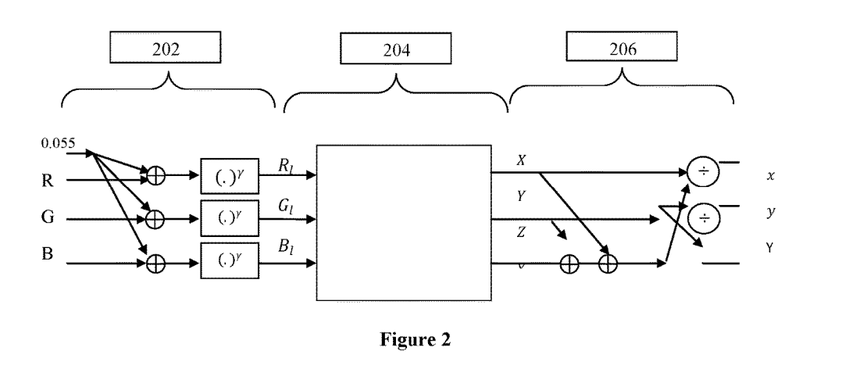
FIG. 2 illustrates an exemplary scheme to convert each RGB pixel in to xyY representation in accordance with an embodiment of the present disclosure.
Figure 3:
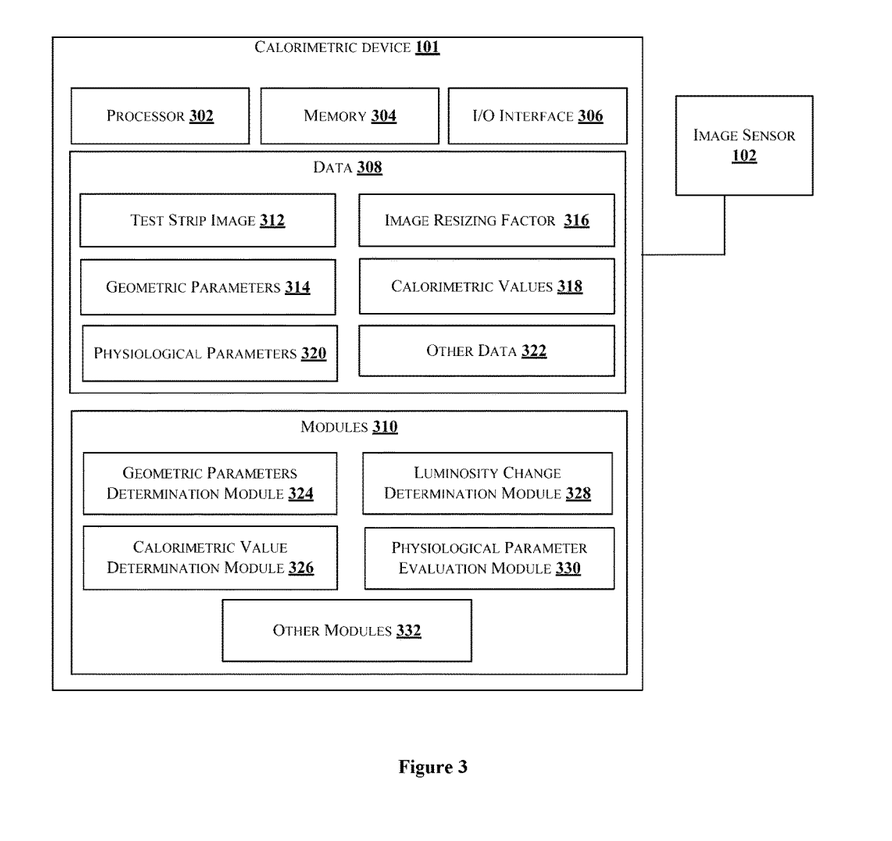
FIG. 3 illustrates an exemplary block diagram of a calorimetric device in accordance with some embodiments of the present disclosure.

In one embodiment, the calorimetric device 101 is configured to determine physiological parameters based on colorimetric curve derived from calorimetric values associated with the captured images of the test strip 108. FIG. 2 illustrates an exemplary scheme to convert each RGB pixel of the captured images into colorimetric values in xyY representation. The calorimetric device 101 is a typical calorimetric device connected with the image sensor 102 as illustrated in FIG. 3. The calorimetric device 101 comprises a processor 302, a memory 304, and an I/O interface 306. The I/O interface 306 is coupled with the processor 302 and an I/O device. The I/O device is configured to receive inputs via the I/O interface 306 and transmit outputs for displaying in the I/O device via the I/O interface 306.

The calorimetric device 101 further comprises data 308 and modules 310. In one implementation, the data 308 and the modules 310 may be stored within the memory 304. In one example, the data 308 may include test strip image 312, geometric parameters 314, image resizing factor 316, calorimetric values 318, physiological parameters 320 and other data 322. In one embodiment, the data 308 may be stored in the memory 304 in the form of various data structures. Additionally, the aforementioned data can be organized using data models, such as relational or hierarchical data models. The other data 218 may be also referred to as reference repository for storing recommended implementation approaches as reference data. The other data 322 may also store data, including temporary data and temporary files, generated by the modules 310 for performing the various functions of the calorimetric device 101.

The modules 310 may include, for example, a geometric parameters determination module (GPDM) 324, a calorimetric value determination module (CVDM) 326, a luminosity change determination module (LCDM) 328 and a physiological parameter evaluation module (PPEM) 330. The modules 310 may also comprise other modules 332 to perform various miscellaneous functionalities of the calorimetric device 101. It will be appreciated that such aforementioned modules may be represented as a single module or a combination of different modules. The modules 310 may be implemented in the form of software, hardware and/or firmware.

Figure 4:
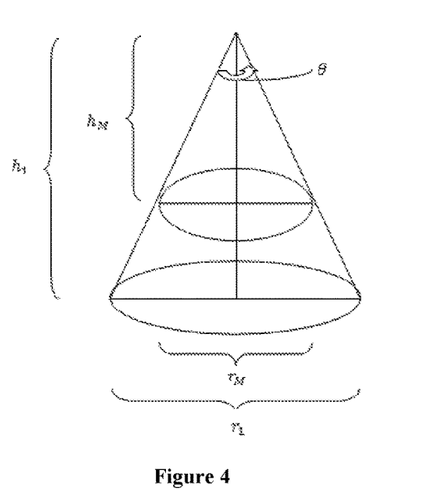
FIG. 4 illustrates an exemplary representation of geometric parameters involved in capturing an image in accordance with an embodiment of the present disclosure.

In operation, the calorimetric device 101 is configured to receive factory calibrated calorimetric values of the test strip 108. The calorimetric device 101 is further configured to receive the first and the second images 312 of the test strip 108 from the image sensor 102 and determine geometric parameters associated with the test strip 108. In one embodiment, the GPDM 324 determines one or more geometric parameters 314 of the test strip 108 associated with the captured first and second images 312 of the test strip 108. FIG. 4 illustrates an exemplary representation of geometric parameters involved in capturing the first and second images 312 of the test strip 108.

In one embodiment, the GPDM 324 obtains a third image by extracting the image portion corresponding to the test strip 108 from the captured first image and determine a plurality of first geometric parameters associated with the third image thus obtained. In one example, the first geometric parameters may include radius $r_1$, length $l_a$, breadth $b_a$, or area $A_a$, perimeter $P_a$, of the test strip 108 associated with the third image. The GPDM 324 further obtains a fourth image by extracting the image portion corresponding to the test strip 108 from the captured second image and determine a plurality of second geometric parameters associated with the fourth image thus obtained. In one example, the second geometric parameters may include radius $r_M$, length $l_b$, breadth $b_b$, or area $A_b$, perimeter $P_b$, of the test strip 108 associated with the fourth image. Based on the plurality of first and second geometric parameters thus determined, the calorimetric device 101 derives the image resizing factor 316 to generate one of a resized first and a resized second image.

In one embodiment, the CVDM 326 determines the image resizing factor $316_{Sb}$ based on the comparison of the plurality of the first and the second geometric parameters 314 as illustrated below.

$$s_b = \frac{l_a}{l_b} \text{ if } l_a > l_b \text{ otherwise } s_b = \frac{l_b}{l_a} \text{ or}$$

$$s_b = \frac{b_a}{b_b} \text{ if } b_a > b_b \text{ otherwise } s_b = \frac{b_b}{b_a} \text{ or}$$

$$s_b = \frac{A_a}{A_b} \text{ if } A_a > A_b \text{ otherwise } s_b = \frac{A_b}{A_a} \text{ or}$$

$$s_b = \frac{P_a}{P_b} \text{ if } P_a > P_b \text{ otherwise } s_b = \frac{P_b}{P_a}$$

In one embodiment, if the image resizing factor $s_b$ 316 is determined to be equal to '1', then the CVDM 326 performs no resizing of the second image. In another embodiment, if the image resizing factor 316$_{Sb}$ is determined to exceed value '1', then the CVDM 326 obtains resized new image $I_b$ based on the image resizing or scale factor 316 and any appropriate interpolation technique. The CVDM 326 is further configured to determine calorimetric vales 318 from one of the resized first and second images. In one embodiment, the CVDM 326 derives one or more RGB pixel values associated with each pixel of the resized first and the resized second image and determines a plurality of device dependent pixel values of the resized first and the resized second images based on each of the one or more derived RGB pixel values.

The CVDM 326 determines the plurality of device dependent pixel values of the resized first and the resized second images by normalizing and applying gamma correction technique. In one aspect, the CVDM 326 normalizes the one or more derived RGB pixel values based on predetermined reference pixel values for example, 100 pixels, to obtain one or more normalized RGB pixel values ($R_c$ $G_c$ $B_c$). Upon normalization, the CVDM 326 calculates intensity value (c) of each of the one or more derived RGB pixel values based on a predetermined gamma correction factor represented in terms of a predetermined intensity value. In one example, the predetermined gamma correction factor is chosen within the range of 1.7 to 2.7. Gamma correction factor represented in terms of predetermined intensity value enables low number of computations during the conversion of device dependent pixel values into device independent pixel values. Based on the intensity value of each of the one or more derived RGB pixel values thus calculated, the CVDM 326 determines one or more linearized gamma corrected device dependent RGB pixel values ($R_l$ $G_l$ $B_l$) corresponding to each of the one or more normalized RGB pixel values ($R_c$ $G_c$ $B_c$).

In one example, the CVDM 326 determines the linearized gamma corrected device dependent RGB pixel values ($R_l$ $G_l$ $B_l$) for each of the one or more normalized RGB pixel values from the reference set ($R_c$ $G_c$ $B_c$) obtained using the transformation described below in equation (1):

$$\begin{bmatrix} R_l \\ G_l \\ B_l \end{bmatrix} = \frac{1}{(0.055)^{2.4}} \begin{bmatrix} (0.055 + R_c)^{2.4} \\ (0.055 + G_c)^{2.4} \\ (0.055 + B_c)^{2.4} \end{bmatrix} \quad (1)$$

As illustrated in equation (1), the predetermined gamma correction factor is 2.4.

Upon determining the linearized gamma corrected device dependent RGB pixel values ($R_l$ $G_l$ $B_l$), the CVDM 326 converts the plurality of linearized gamma corrected device dependent pixel values into a corresponding device independent pixel values (X Y Z) associated with the resized first and the resized second images using the transformation as illustrated below in equation (2):

$$\begin{bmatrix} X \\ Y \\ Z \end{bmatrix} = \begin{bmatrix} 434.95 & 377.16 & 190.37 \\ 224.22 & 754.32 & 76.149 \\ 20.356 & 1054.7 & 20.356 \end{bmatrix} \begin{bmatrix} R_l \\ G_l \\ B_l \end{bmatrix} \quad (2)$$

The CVDM 326 then determines the first and the second calorimetric values 318 represented in 3-D chromaticity model (x y Y) using the transformation as illustrated below in equation (3):

$$\begin{bmatrix} x \\ y \\ Y \end{bmatrix} = \begin{bmatrix} X/(X+Y+Z) \\ Y/(X+Y+Z) \\ Y \end{bmatrix} \quad (3)$$

Figure 5:
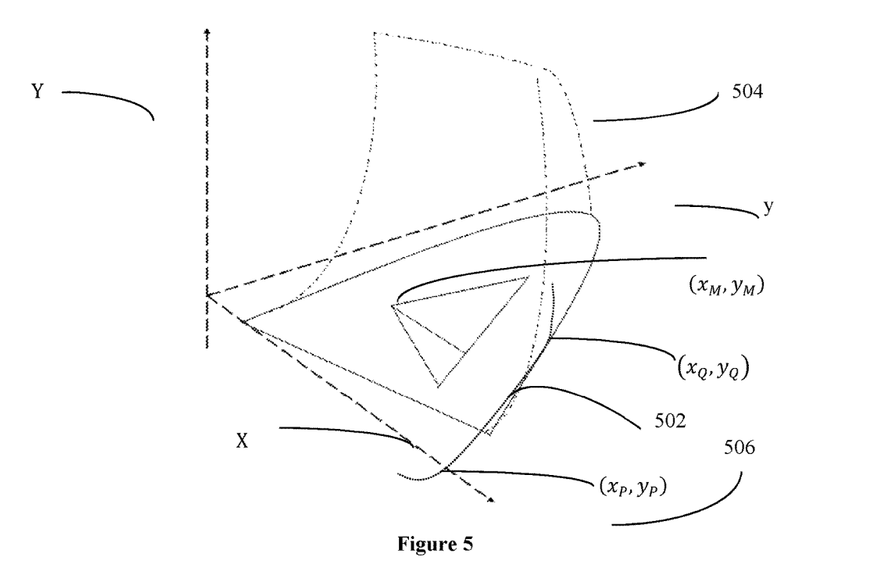
FIG. 5 illustrates an exemplary 3D representation of chromaticity xyY model in accordance with an embodiment of the present disclosure.

Upon determining the first and the second calorimetric values, the LCDM 328 determines the change in luminosity based on the first and the second calorimetric values 318. In one embodiment, the LCDM 328 generates a calibration curve corresponding to each of the first and the second calorimetric values 318 and determines a corresponding first and a second luminosity values. In one example, the exemplary 3D representation of chromaticity xyY model corresponding to one of the first and the second calorimetric values is illustrated in FIG. 5. The curve 502 represents the Calibration curve (indicative curve) of intended test fluid and the curve 504 represents the luminance value of 2-D chromaticity point in (xy) space. Further, the curve 506 represents the xy space.

Figure 6:
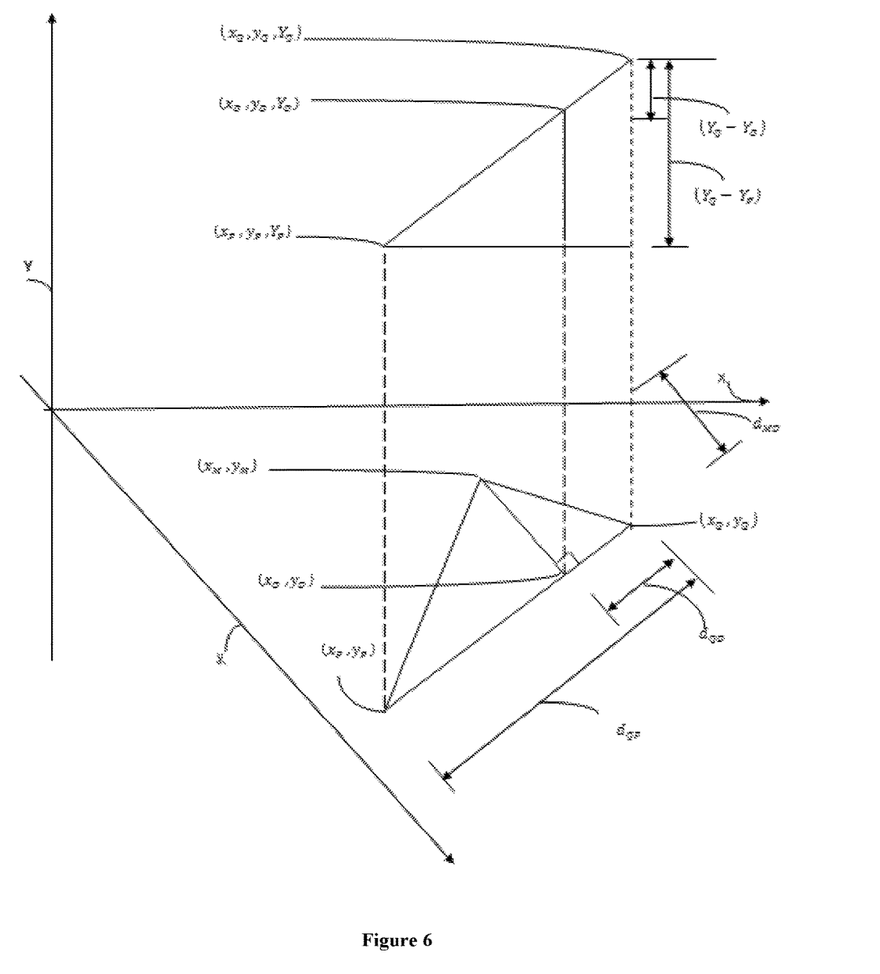
FIG. 6 illustrates an exemplary geometrical representation of calibration and determination of color calorimetry in accordance with an embodiment of the present disclosure.

As illustrated in FIG. 5, consider the point M with a coordinate ($x_M$, $y_M$) that is obtained from a measurement made using the test strip 108. Two points P and Q are identified with corresponding co-ordinate points ($x_P$, $y_P$) and ($x_Q$, $y_Q$) belonging to calibrated and stored curve is obtained by searching two nearest points to the just measured point ($x_M$, $y_M$) in the chromaticity space (xy) as shown in FIG. 5 and FIG. 6. FIG. 6 illustrates an exemplary geometrical representation of calibration and determination of color calorimetry. In order to find appropriate chromaticity point ($x_O$, $y_O$) belonging to calibration curve as shown in FIG. 6, a triangle is formed with vertices points ($x_P$, $y_P$), ($x_Q$, $y_Q$) and ($x_M$, $y_M$) as shown in FIG. 5 and FIG. 6.

The LCDM 328 is configured to determine the distance $d_{QP}$ between the two points ($x_P$, $y_P$) and ($x_Q$, $y_Q$) and determine the orthogonal distance $d_{MO}$ to the measured point ($x_M$, $y_M$) and line joining points ($x_P$, $y_P$) and ($x_Q$, $y_Q$). Based on the determined distance $d_{QP}$ and the orthogonal distance $d_{MO}$, the LCDM 328 determines the first luminosity value in 3D-chromaticity point ($x_P$, $y_P$, $Y_P$) and point ($x_Q$, $y_Q$, $Y_Q$) projecting from 2-D Chromaticity point ($x_P$, $y_P$) and point ($x_O$, $y_O$), respectively. The LCDM 328 further determines the second luminosity value in 3D Chromaticity point ($x_O$, $y_O$, $Y_O$) projected from 2-D chromaticity point ($x_O$, $y_O$) which is derived out of points ($x_M$, $y_M$), ($x_Q$, $y_Q$) ($x_P$, $y_P$) and ($x_Q$, $y_Q$). Using the computed first and second luminosity values, the LCDM 328 determines the difference in luminosity based on which the one or more physiological parameters 320 are determined. In one embodiment, the PPEM 330 determines the one or more physiological parameters 320 based on the respective calibration curves, associated difference in luminosity values and predetermined calorimetric values determined at the time of manufacturing.

Thus, the calorimetric device 101 determines the physiological parameter associated with the test fluid with low number of computations, involving less time and memory.

Figure 7:
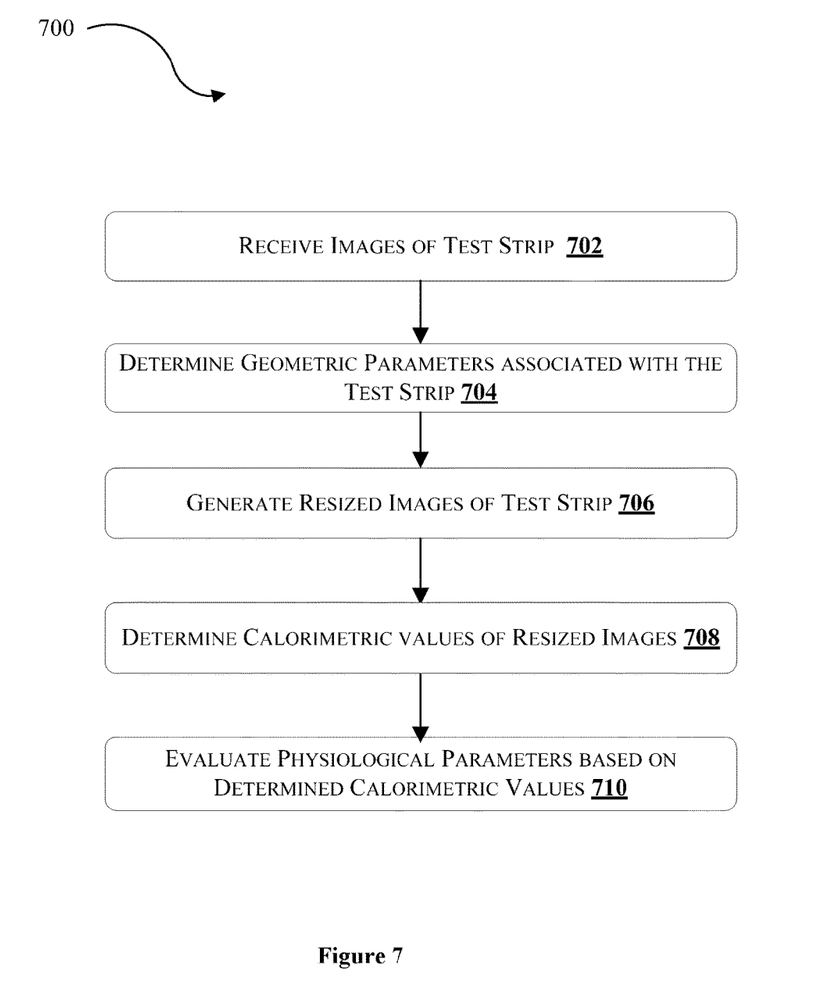
FIG. 7 illustrates a flowchart of an exemplary method of performing colorimetric analysis of a test fluid to evaluate associated physiological parameters in accordance with some embodiments of the present disclosure.

FIG. 7 illustrates a flowchart of a method of performing colorimetric analysis of a test fluid to evaluate associated physiological parameters in accordance with some embodiments of the present disclosure.

As illustrated in FIG. 7, the method 700 comprises one or more blocks implemented by the processor 302 for performing colorimetric analysis of a test fluid to evaluate associated physiological parameters. The method 700 may be described in the general context of computer executable instructions. Generally, computer executable instructions can include routines, programs, objects, components, data structures, procedures, modules, and functions, which perform particular functions or implement particular abstract data types.

The order in which the method 700 is described is not intended to be construed as a limitation, and any number of the described method blocks can be combined in any order to implement the method 700. Additionally, individual blocks may be deleted from the method 700 without departing from the spirit and scope of the subject matter described herein. Furthermore, the method 700 can be implemented in any suitable hardware, software, firmware, or combination thereof.

At block 702, receive images of test strip. In one embodiment, the calorimetric device 101 is configured to receive factory calibrated calorimetric values of the test strip 108. The calorimetric device 101 is further configured to receive the first and the second images 312 of the test strip 108 from the image sensor 102 and determine geometric parameters associated with the test strip 108.

At block 704, determine geometric parameters associated with the test strip. In one embodiment, the GPDM 324 obtains a third image by extracting the image portion corresponding to the test strip 108 from the captured first image and determine a plurality of first geometric parameters associated with the third image thus obtained. In one example, the first geometric parameters may include radius $r_1$, length $l_a$, breadth $b_a$, or area $A_a$, perimeter $P_a$, of the test strip 108 associated with the third image. The GPDM 324 further obtains a fourth image by extracting the image portion corresponding to the test strip 108 from the captured second image and determine a plurality of second geometric parameters associated with the fourth image thus obtained. In one example, the second geometric parameters may include radius $r_M$, length $l_b$, breadth $b_b$, or area $A_b$, perimeter $P_b$, of the test strip 108 associated with the fourth image. Based on the plurality of first and second geometric parameters thus determined, the calorimetric device 101 derives the image resizing factor 316 to generate one of a resized first and a resized second image.

At block 706, generate resized images of test strip. In one embodiment, the CVDM 326 determines the image resizing factor $316_{Sb}$ based on the comparison of the plurality of the first and the second geometric parameters 314 and generates resized images based on the image resizing factor 316. In one embodiment, if the image resizing factor $s_b 316$ is determined to be equal to '1', then the CVDM 326 performs no resizing of the second image. In another embodiment, if the image resizing factor $316_{Sb}$ is determined to exceed value '1', then the CVDM 326 obtains resized new image $I_b$ based on the image resizing or scale factor 316 and any appropriate interpolation technique.

At block 708, determine calorimetric values of resized images. In one embodiment, the CVDM 326 is configured to determine calorimetric vales 318 from one of the resized first and second images. In one embodiment, the CVDM 326 derives one or more RGB pixel values associated with each pixel of the resized first and the resized second image and determines a plurality of device dependent pixel values of the resized first and the resized second images based on each of the one or more derived RGB pixel values.

The CVDM 326 determines the plurality of device dependent pixel values of the resized first and the resized second images by normalizing and applying gamma correction technique. In one aspect, the CVDM 326 normalizes the one or more derived RGB pixel values based on predetermined reference pixel values for example, 100 pixels, to obtain one or more normalized RGB pixel values ($R_c$ $G_c$ $B_c$). Upon normalization, the CVDM 326 calculates intensity value (c) of each of the one or more derived RGB pixel values based a predetermined gamma correction factor represented in terms of a predetermined intensity value. In one example, the predetermined gamma correction factor is within the range of 1.7 to 2.7. Gamma correction factor represented in terms of predetermined intensity value enables low number of computations during the conversion of device dependent pixel values into device independent pixel values. Based on the intensity value of each of the one or more derived RGB pixel values thus calculated, the CVDM 326 determines one or more linearized gamma corrected device dependent RGB pixel values ($R_l$ $G_l$ $B_l$) corresponding to each of the one or more normalized RGB pixel values ($R_c$ $G_c$ $B_c$).

In one example, the CVDM 326 determines the linearized gamma corrected device dependent RGB pixel values ($R_l$ $G_l$ $B_l$) for each the one or more normalized RGB pixel values from the reference set ($R_c$ $G_c$ $B_c$) obtained. Upon determining the linearized gamma corrected device dependent RGB pixel values ($R_l$ $G_l$ $B_l$), the CVDM 326 converts the plurality of linearized gamma corrected device dependent pixel values into a corresponding device independent pixel values (X Y Z) associated with the resized first and the resized second images.

At block 710, evaluate physiological parameters based on determined calorimetric values. In one embodiment, the PPEM 330 determines the one or more physiological parameters 320 based on the respective calibration curves and associated difference or change in luminosity values. The LCDM 328 determines the change in luminosity based on the first and the second calorimetric values 318. In one embodiment, the LCDM 328 generates a calibration curve corresponding to each of the first and the second calorimetric values 318 and determines a corresponding first and a second luminosity values. The PPEM 330 determines the one or more physiological parameters 320 based on the respective calibration curves, associated difference in luminosity values and predetermined calorimetric values determined at the time of manufacturing. Thus, the calorimetric device 101 determines the physiological parameter associated with the test fluid with low number of computations, involving less time and memory.

As described above, the modules 310, amongst other things, include routines, programs, objects, components, and data structures, which perform particular tasks or implement particular abstract data types. The modules 310 may also be implemented as, signal processor(s), state machine(s), logic circuitries, and/or any other device or component that manipulate signals based on operational instructions. Further, the modules 310 can be implemented by one or more hardware components, by computer-readable instructions executed by a processing unit, or by a combination thereof.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., are non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

The invention claimed is:

1. A method of performing colorimetric analysis of a test fluid to evaluate associated physiological parameters, said method comprising:
    receiving, by a processor of a colorimetric device, a first image of a test strip captured at a first height before dipping the test strip into the test fluid, and a second image of the test strip captured at a second height after dipping the test strip into the test fluid;
    determining, by the processor, a plurality of first and second geometric parameters respectively associated with the test strip based on analysis of the captured first and second images;
    deriving, by the processor, an image resizing factor based on the plurality of first and second geometric parameters and generating one of a resized first image and a resized second image based on the image resizing factor thus derived;
    determining, by the processor, first and second colorimetric values respectively associated with the resized first and the resized second images by:
        deriving one or more RGB pixel values associated with each pixel of the resized first and the resized second image;
        determining a plurality of device dependent pixel values of the resized first and the resized second images based on each of the one or more derived RGB pixel values;
        converting the plurality of device dependent pixel values thus determined into a corresponding device independent pixel values associated with the resized first and the resized second images; and
        determining the first and second colorimetric values associated with the resized first and the resized second images upon conversion; and
    evaluating, by the processor, one or more physiological parameters associated with the test fluid based on change in luminosity determined based on the one or more predetermined colorimetric values, the one or more first and the second colorimetric values.

2. The method as claimed in claim 1, wherein the step of determining the plurality of device dependent pixel values of the resized first and the resized second images comprising the steps of:
    normalizing the one or more derived RGB pixel values based on predetermined reference pixel values to obtain one or more normalized RGB pixel values;
    calculating intensity value (c) of each of the one or more derived RGB pixel values based a predetermined gamma correction factor represented in terms of a predetermined intensity value; and
    determining one or more linearized gamma corrected device dependent RGB pixel values corresponding to each of the one or more normalized RGB pixel values based on the intensity value of each of the one or more derived RGB pixel values thus calculated.

3. The method as claimed in claim 2, wherein the predetermined gamma correction factor is chosen within the range of 1.7 to 2.7.

4. The method as claimed in claim 1, wherein the step of determining the plurality of first and second geometric parameters respectively associated with the captured first and second images, comprising the steps of:
    obtaining a third image by extracting the image portion corresponding to the test strip from the captured first image;
    determining the plurality of first geometric parameters of the test strip from the third image thus obtained;
    obtaining a fourth image by extracting the image portion corresponding to the test strip from the captured second image; and
    determining the plurality of second geometric parameters of the test strip from the fourth image thus obtained.

5. The method as claimed in claim 4, wherein the step of deriving the image resizing factor and generating one of the resized first and the resized second images, comprising:
    comparing the plurality of first geometric parameters associated with the third image with the plurality of second geometric parameters associated with the fourth image;
    determining the image resizing factor based on the comparison;
    generating the resized first image by scaling up the first image based on the image resizing factor upon determining that the image resizing factor is equal to unity; and
    generating the resized second image by scaling up the second image based on the image resizing factor upon determining that the image resizing factor exceeds unity.

6. The method as claimed in claim 1, wherein the step of deriving the image resizing factor and generating one of the resized first and the resized second images, comprising:

comparing the plurality of first geometric parameters associated with the third image with the plurality of second geometric parameters associated with the fourth image;
determining the image resizing factor based on the comparison;
generating the resized first image by scaling up the first image based on the image resizing factor upon determining that the image resizing factor is equal to unity; and
generating the resized second image by scaling up the second image based on the image resizing factor upon determining that the image resizing factor exceeds unity.

7. The method as claimed in claim 1, wherein the step of determining the change in luminosity, comprising:
determining a calibration curve corresponding to each of the first and the second colorimetric values;
obtaining a first and a second three-dimensional chromaticity point on the calibrated curve proximal to the each of the first and second colorimetric values;
determining a first luminosity value based on the first and the second three-dimensional chromaticity points associated with the first colorimetric values;
determining a second luminosity value based on the first and the second three-dimensional chromaticity points associated with the second colorimetric values; and
calculating the change in luminosity based on the comparison of the first and the second luminosity values thus determined.

8. A colorimetric device for performing colorimetric analysis of a test fluid to evaluate associated physiological parameters, said device comprising:
an image capturing device configured to capture one or more images of a test strip;
a processor coupled with the image capturing device; and
a memory disposed in communication with the processor for storing processor-executable instructions, the instructions causing the processor to:
receive a first image of the test strip captured by the image capturing device at a first height before dipping the test strip into the test fluid, and a second image of the test strip captured at a second height after dipping the test strip into the test fluid;
determine a plurality of first and second geometric parameters respectively associated with the test strip based on analysis of the captured first and second image;
derive an image resizing factor based on the plurality of first and second geometric parameters and generating one of a resized first image and a resized second image based on the image resizing factor thus derived;
determine a first and second colorimetric value respectively associated with the resized first and the resized second image by:
deriving one or more RGB pixel values associated with each pixel of the resized first and the resized second images;
determining a plurality of device dependent pixel values of the resized first and the resized second image based on each of the one or more derived RGB pixel values;
converting the plurality of device dependent pixel values thus determined into a corresponding device independent pixel values associated with the resized first and the resized second images; and
determining the one or more first and second colorimetric values associated with the resized first and the resized second image upon conversion; and
evaluate one or more physiological parameters associated with the test fluid based on change in luminosity determined based on the one or more predetermined colorimetric values, the one or more first and the second colorimetric values.

9. The device as claimed in claim 8, wherein the processor is configured to determine the plurality of device dependent pixel values of the resized first and the resized second images by performing the steps of:
normalizing each of the one or more derived RGB pixel values based on predetermined reference pixel values to obtain one or more normalized RGB pixel values for each of the one or more derived RGB pixel values;
calculating intensity value (c) of each of the one or more derived RGB pixel values based on a predetermined gamma correction factor represented in terms of a predetermined intensity value; and
determining one or more linearized gamma corrected device dependent RGB pixel values corresponding to each of the one or more normalized RGB pixel values based on the intensity value of each of the one or more derived RGB pixel values thus calculated.

10. The device as claimed in claim 9, wherein the processor is configured to choose the predetermined gamma correction factor within the range of 1.7 to 2.7.

11. The device as claimed in claim 8, wherein the processor is configured to determine the plurality of first and second geometric parameters respectively associated with the captured first and second image by performing the steps of:
obtaining a third image by extracting the image portion corresponding to the test strip from the captured first image;
determining the plurality of first geometric parameters of the test strip from the third image thus obtained;
obtaining a fourth image by extracting the image portion corresponding to the test strip from the captured second image; and
determining the plurality of second geometric parameters of the test strip from the fourth image thus obtained.

12. The device as claimed in claim 11, wherein the processor is configured to derive the image resizing factor and generate one of the resized first and the resized second image, by the steps of:
comparing the plurality of first geometric parameters associated with the third image with the plurality of second geometric parameters associated with the fourth image;
determining the image resizing factor based on the comparison;
generating the resized first image by scaling up the first image based on the image resizing factor upon determining that the image resizing factor is equal to unity; and
generating the resized second image by scaling up the second image based on the image resizing factor upon determining that the image resizing factor exceeds unity.

13. The device as claimed in claim 8, wherein the processor is configured to derive the image resizing factor and generate one of the resized first and the resized second image, by the steps of:
- comparing the plurality of first geometric parameters associated with the third image with the plurality of second geometric parameters associated with the fourth image;
- determining the image resizing factor based on the comparison;
- generating the resized first image by scaling up the first image based on the image resizing factor upon determining that the image resizing factor is equal to unity; and
- generating the resized second image by scaling up the second image based on the image resizing factor upon determining that the image resizing factor exceeds unity.

14. The device as claimed in claim 8, wherein the processor is configured to determine the change in luminosity by the steps of:
- determining a calibration curve corresponding to each of the first and the second colorimetric values;
- obtaining a first and a second three-dimensional chromaticity point on the calibrated curve proximal to the each of the first and second colorimetric values;
- determining a first luminosity value based on the first and the second three-dimensional chromaticity points associated with the first colorimetric values;
- determining a second luminosity value based on the first and the second three-dimensional chromaticity points associated with the second colorimetric values; and
- calculating the change in luminosity based on the comparison of the first and the second luminosity values thus determined.

* * * * *